United States Patent [19]

Cerny et al.

[11] Patent Number: 4,807,676
[45] Date of Patent: Feb. 28, 1989

[54] FLUID TRANSFER WORKSTATION

[75] Inventors: David E. Cerny, Crystal Lake; David V. Bacehowski, Wildwood; John T. Foley, Wheeling, all of Ill.

[73] Assignee: Baxter International Inc., Deerfield, Ill.

[21] Appl. No.: 705,578

[22] Filed: Feb. 26, 1985

[51] Int. Cl.$^4$ ............................................. B01D 13/00
[52] U.S. Cl. ........................................ 141/98; 141/83; 604/6; 210/96.1
[58] Field of Search .................... 210/95, 136, 927; 141/98, 83; 604/4, 5, 6

[56] References Cited

U.S. PATENT DOCUMENTS

| | | | |
|---|---|---|---|
| 2,702,034 | 2/1955 | Walter | 604/262 |
| 3,064,647 | 11/1962 | Earl | 424/101 |
| 3,986,506 | 10/1976 | Garber et al. | 210/927 X |
| 3,986,508 | 10/1976 | Barrington | 604/411 |
| 4,022,256 | 5/1977 | Berkman et al. | 141/1 |
| 4,157,723 | 6/1979 | Granzow et al. | 141/1 |
| 4,197,847 | 4/1980 | Djerassi | 128/214 |
| 4,223,675 | 9/1980 | Williams | 604/410 |
| 4,350,585 | 9/1982 | Johansson et al. | 210/927 X |
| 4,356,394 | 10/1982 | Cobean et al. | 250/347 |
| 4,582,598 | 4/1986 | Bilstad et al. | 210/433.2 X |

Primary Examiner—Henry J. Recla
Assistant Examiner—Edward Donovan
Attorney, Agent, or Firm—Paul C. Flattery; Bradford R. L. Price; Paul M. Vargo

[57] ABSTRACT

A workstation for use in processing units of blood into components includes hangers for supporting the primary and transfer containers usable to store and transport the blood components, an optical sensor for sensing the outflow of red blood cells from the primary container, electrically actuated solenoid clamps for selectively opening and closing flow lines from an additive container and flow lines to the transfer containers. Electrically controlled radiant energy sources can be used to provide sterile flow connections where sterile connectors are joined together to form the blood component transfer set.

3 Claims, 6 Drawing Sheets

FLUID TRANSFER WORKSTATION

BACKGROUND OF THE INVENTION

The invention pertains to workstations for use in processing collected body fluids. More particularly the invention pertains to a workstation for processing units of collected human blood into components.

The collection and processing of human blood into components has made use of integrally formed sterile two and three bag blood collection sets. Two bag sets include two containers formed as a closed sterile system into which blood components can be separated. A three bag set has included three integrally formed sterile containers including a primary container and two transfer containers. The processing of a unit of blood, previously collected into the primary container, has involved centrifuging and separating blood components into the secondary container or containers.

Blood collection sets have now become available which are not integrally formed as complete sets but rather are components which can be joined together and converted into a sterile closed system through the use of radiant energy. However, such sets require a more systematic and organized approach to the processing steps than has heretofore been necessary with integrally formed sets. One such set including a sterile connector, is disclosed in U.S. Pat. No. 4,223,675, entitled "Solution Containers Such as Blood Bags and System for Preparing Same," issued to Baxter Travenol Laboratories, Inc. An alternate form of sterile connector is disclosed in U.S. Pat. No. 4,022,256 entitled "Aseptic Fluid Transfer System which issued May 10, 1977.

SUMMARY OF THE INVENTION

In accordance with the invention a workstation for processing a selected corporal fluid, such as blood, collected in a primary container includes means for supporting the primary container, means for supporting a secondary container coupled to the primary container, means connected to the primary container supporting means for compressing the primary container, means for sensing the flow of a selected fluid from the primary container to the secondary container in response to the compressing means acting thereon and means for closing the flow path coupling the containers in response to the selected fluid flow being sensed by the sensing means. The invention further provides for the use of manually operable compressing means or, alternately, means for activating the compressing means.

In a further embodiment of the invention, means are provided for supporting an additive container coupled to the primary container by a flow path, as well as means for closing the flow path from the additive container and means coupled to the closing means for selective activation thereof. The means for closing can include means for clamping a flexible conduit closed. The means for closing can be an electrically activated solenoid clamp.

In yet another embodiment of the invention, means are provided for forming a sterile fluid flow path between the primary and the secondary container. The means for forming can include electrically activated means for generating radiant energy for forming the sterile flow path.

In accordance with the invention, a method is provided for processing a corporal fluid previously collected in a primary container. The method includes the steps of supporting the container to permit the flow of fluid therefrom, forming a sealed, sterile, fluid flow path between the primary container and a secondary container, compressing the primary container to force fluid therefrom into the secondary container, sensing a selected flow of fluid from the primary container and closing the fluid flow path between the containers in response to the selected fluid flow having been sensed.

DETAILED DESCRIPTION

Figure 1:
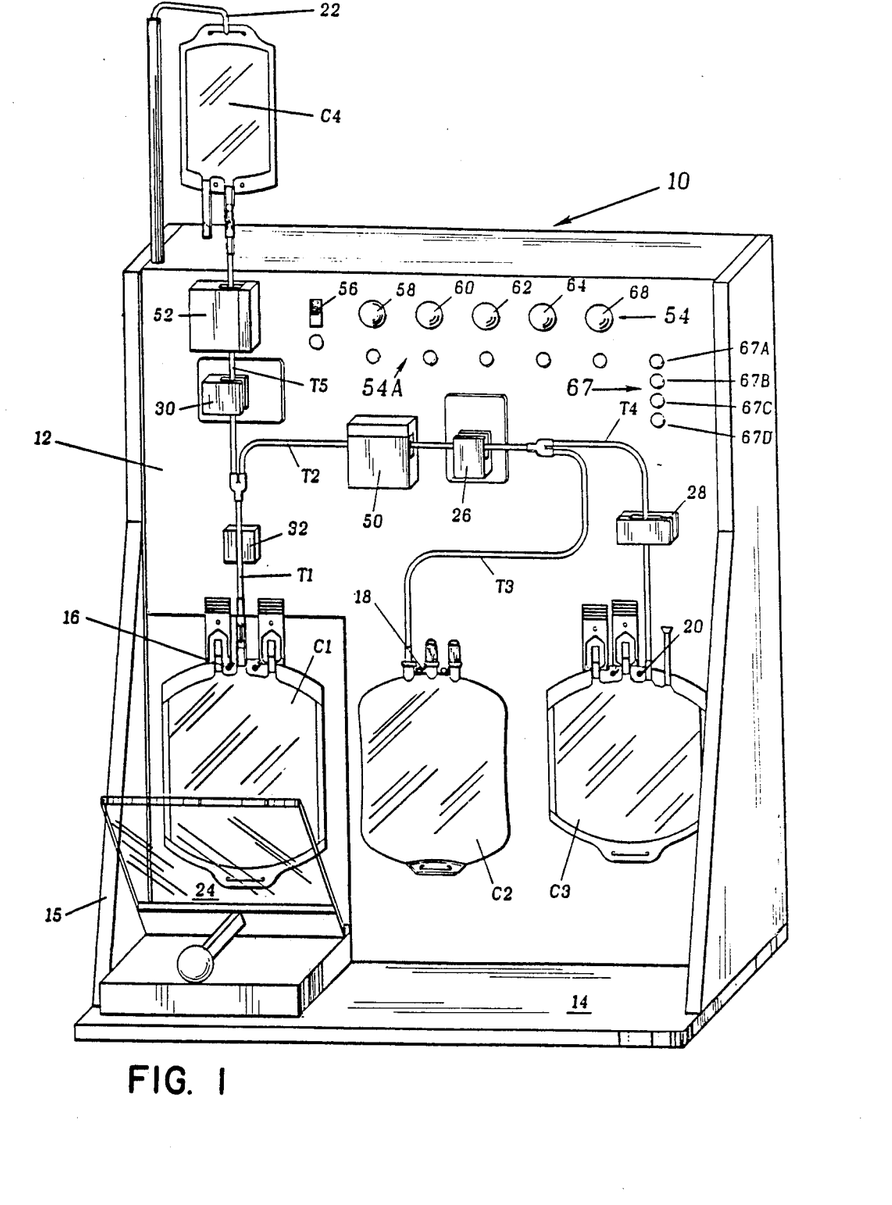
FIG. 1 is a perspective view of a workstation embodying the present invention.

With respect to the figures, FIG. 1 illustrates a workstation 10 intended for general use in processing corporal fluids, such as blood, which have been previously withdrawn from a selected body. In the withdrawing process the blood is initially collected in a primary container C1. The container C1 is usually part of a sealed, sterile, system. The workstation 10 includes an essentially vertical supporting plate or member 12, a pair of side plates 15 and an essentially horizontal lower member 14. The side plates 13 function not only to provide stability to the workstation 10 but also to confine the processing steps within the workstation 10.

Affixed to the vertical rear panel 12, is a hanger 16 on which the primary blood filled container C1 may be hung and supported during the ensuing processing operations. As part of the processing operations it is often necessary to transfer components of blood from the primary container C1 to a secondary or transfer container such as C2. Also affixed to the essentially vertical member 12 is a hanger 18 from which the transfer container C2 may be hung or supported during processing. With respect to those situations where a second transfer container C3 is necessary, a hanger 20 is affixed to the vertical member 12 for purposes of supporting the second transfer container C3.

Under normal blood collection practices the primary container C1 contains previously drawn blood that would have been put through a centrifuge to separate the blood into components. The container C1 would then be mounted on the hanger 16. Using conventional blood collection sets, the primary container C1 would have integrally associated therewith one or perhaps two transfer containers, such as C2, C3, which would be coupled by flexible hollow conduits T1, T2, T3, and T4 to the primary container C1. Additionally, it is well known in the art for conventional blood collection sets to have associated with the primary container C1, an additive container C4. The additive container has a breakable internal seal, or frangible, so that the additive can be mixed with blood components at the appropriate time during the processing. The additive container C4 is conventionally coupled to the primary container C1 through the flexible plastic conduits T5 and T1.

The workstation 10 includes a hanger 22 from which the additive container C4 may be supported during the processing phase. The hanger 22 is positioned above the vertical member 12 so that the additive will readily flow downward into the primary container supported by the hanger 16. A three or four bag set including the additive container, the primary container and one or two transfer containers is conventionally formed as an integral sterile system with each of the containers C1-C4 being linked by flexible plastic conduit T1-T5. Such a four bag collection set with interconnecting flexible conduits T1-T5 is shown installed in the workstation 10 of FIG. 1.

As part of the conventional processing of a unit of blood, the primary container is usually centrifuged to separate the red blood cells from the plasma and platelets. Once the centrifuging has been completed the set is then placed on the workstation 10 as indicated in FIG. 1. A plasma extractor 24, a spring loaded clamp, is affixed to the workstation 10 adjacent to the primary container hanger 16 for the purpose of applying pressure to or compressing the primary container C1 thereby forcing the lighter platelets and plasma out the top of the primary container C1. The plasma flows through the interconnecting tubing sections T1, T2 and T3 into the transfer container C2. Alternately, a flexible bladder or cylinder that could be automatically inflated could be used to apply pressure to the primary container C1.

Affixed to the vertical member 12 is a clamp 26, in FIG. 1, which can be a solenoid actuated pinch clamp. The clamp 26 can be energized to clamp the flexible tubing T2 closed to disconnect container C1 from container C2. Also associated with the vertical member 12 is a clamp 28 which can be a manually operable mechanical clamp or alternately could be a solenoid operated clamp of the type as is clamp 26. The purpose of the clamp 28 is to close off the flexible tubing T4 to the transfer container C3 during processing. Finally, associated with the vertical panel 12 is a third clamp 30, for the purpose of pinching off or clamping the flexible tubing T5 between the primary container C1 and the additive container C4. The clamp 30 is a solenoid actuated clamp which is identical to the clamp 26.

After the blood in the container C1 has been centrifuged and the plasma extractor 24 is activated, either manually or as an electrically controlled device, the primary container C1 is compressed or squeezed forcing the plasma and platelets through the tubing T1. Assuming the clamps 28 and 30 have been activated closing off tubing sections T4 and T5, the plasma and platelets will be forced through tubing T2-T3 into transfer container C2. An optical sensor 32 also affixed to the vertical panel 12 can be used to sense the interface between the lighter weight, pale colored plasma and platelets, and the heavier red blood cells in the primary container C1. Once the red blood cells start to be forced out of the primary container C1 by the plasma extractor 24 a signal can be generated by the optical sensor 32 indicating the presence of the red blood cells in the tubing T1. The signal from the optical sensor 32 can then be used to energize the clamp 26 thereby separating or isolating the transfer container C2 from the primary container C1. At this point in time essentially all of the plasma and platelets will have been transferred into the transfer containers C2.

If desired, or appropriate to the processing step, the plasma extractor 24 can be opened, removing the compression forces from the container C1 and the clamp 30 between the additive container and the primary container can be opened at this time unclamping the tubing T5. The frangible in the additive container C4 can be broken and the additive in the container C4 will flow through the tubing T5, past the clamp 30, and through the tubing T1 into the primary container C1. Once the additive has flowed into the primary container C1 the primary container C1 may be sealed and removed from the rest of the bags in the set.

Container C2 and container C3 can be centrifuged to separate the platelets from the plasma in the container C2. The combined units C2 and C3 can be rehung on the respective hangers 18 and 20 and a second plasma extractor can be used to force the lightweight platelets from the container C2 into the transfer container C3. Alternately, the containers C2 and C3 can be hung on the hangers 16 and 18 respectively and the original plasma extractor 24 can be used to compress the container C2. Once the platelets have been separated from the plasma in the container C2 and the plasma forced into the transfer container C3, the containers C2 and C3 can be sealed and separated from one another using standard radio frequency sealers of a type well known in the art.

A conventional seal formed by the use of RF signals can be made in the tubing to seal the various containers. A standard product sold under the trademark HEMATRON can be used for this purpose.

As an alternate to using the workstation 10 in connection with an integrally formed known set of containers, it is also possible to use the workstation 10 in connection with a set of containers which can be combined at the workstation.

Figure 2:
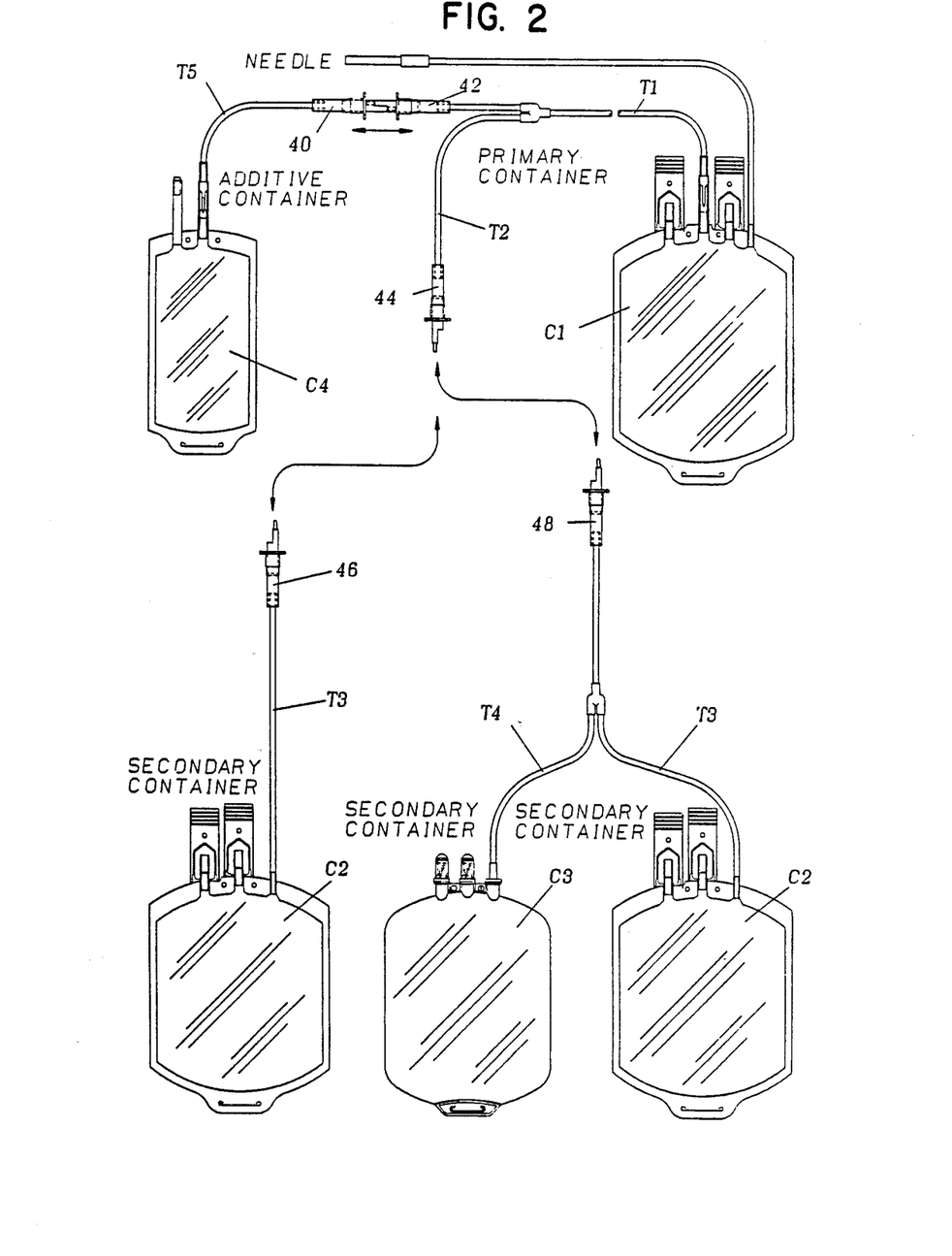
FIG. 2 is a block diagram of one form of a blood collection set usable with the present invention.

FIG. 2 illustrates a collection set of a type which can be assembled at the workstation 10 and which is not an integrally formed unit as known in the prior art. As illustrated in FIG. 2 the collection set includes an additive container, corresponding to the additive container C4, a primary container, corresponding to the primary container C1 and secondary containers, corresponding to the containers C2 and C3, all of which can be interconnected in a selected fashion by means of a plurality of sterile connectors 40 through 48. For example, as illustrated in FIG. 2, the connectors 40 and 42 can be joined together so as to couple the additive container C4 to the primary container C1 via the conduits T5 and T1 respectively. Additionally, the sterile connectors 44 and 48 may be joined together so as to couple the secondary container C2 and C3 to the primary container C1 via the flexible conduits T2, T3 and T4. Also shown in FIG. 2 is a single bag secondary container configuration having an associated sterile connector 46. The connector set shown in FIG. 2 has previously been disclosed in U.S. Pat. No. 4,611,643 filed Nov. 21, 1983, entitled "Interlocking Fluid Transfer Device and Resulting Assembly," and assigned to the assignee of the present application. The disclosure of that patent application is hereby incorporated by reference.

As taught in the above-noted, incorporated, patent application, the connectors such as 40, 42 having been joined together, a sealed sterile connection can be formed therebetween by exposing selected parts of those connectors to radiant energy. Once the connectors have been fused and the seal created due to the heat from the radiant energy, a sealed blood collection set results having the selected number of containers and the desired configuration.

An apparatus for fusing the connectors such as 40,42 together is disclosed in U.S. Pat. No. 4,356,394 entitled "Apparatus for Applying Radiant Beam" which issued Oct. 26, 1982 and was assigned to Baxter Travenol Laboratories, Inc. The disclosure of that patent is hereby incorporated by reference herein. Alternately, the type of sterile connector disclosed in the above-noted U.S. Pat. No. 4,022,256 could be used.

To facilitate creating the sterile seals between the connectors such as 40, 42 and 44, 48, for example, the workstation 10 includes a light nest 50 and a light nest 52. The light nests 50 and 52 include electrically actuated sources of radiant energy as disclosed in the above incorporated patent application for the purpose of fusing sterile connectors, such as the connectors 44, 48 or 40, 42 that have been inserted therein. Hence, the light nest 50 and light nest 52 include receptacles for receiving the connectors to be sealed together and sources for generating the radiant energy which is directed onto the sterile connectors for the purpose of creating the seal. Light nests 50, 52 each include closable doors to keep the radiant energy within the light nest and an optical sensor to sense the presence or absence of the radiant energy.

To assist in carrying out the necessary steps of the processing procedure wherein a connectable set such as shown in FIG. 2 is to be used in connection with the workstation 10 a plurality of switches 54 and indicators 54a and 67, are provided for various purposes as will be discussed subsequently.

An advantage of the structure of the workstation 10 is that, apart from the centrifuge that is necessary to separate the blood components, the necessary clamps and/or sources of radiant energy are assembled together in a way that speeds and facilitates the processing of the blood unit including controlling the additives.

Figure 3:
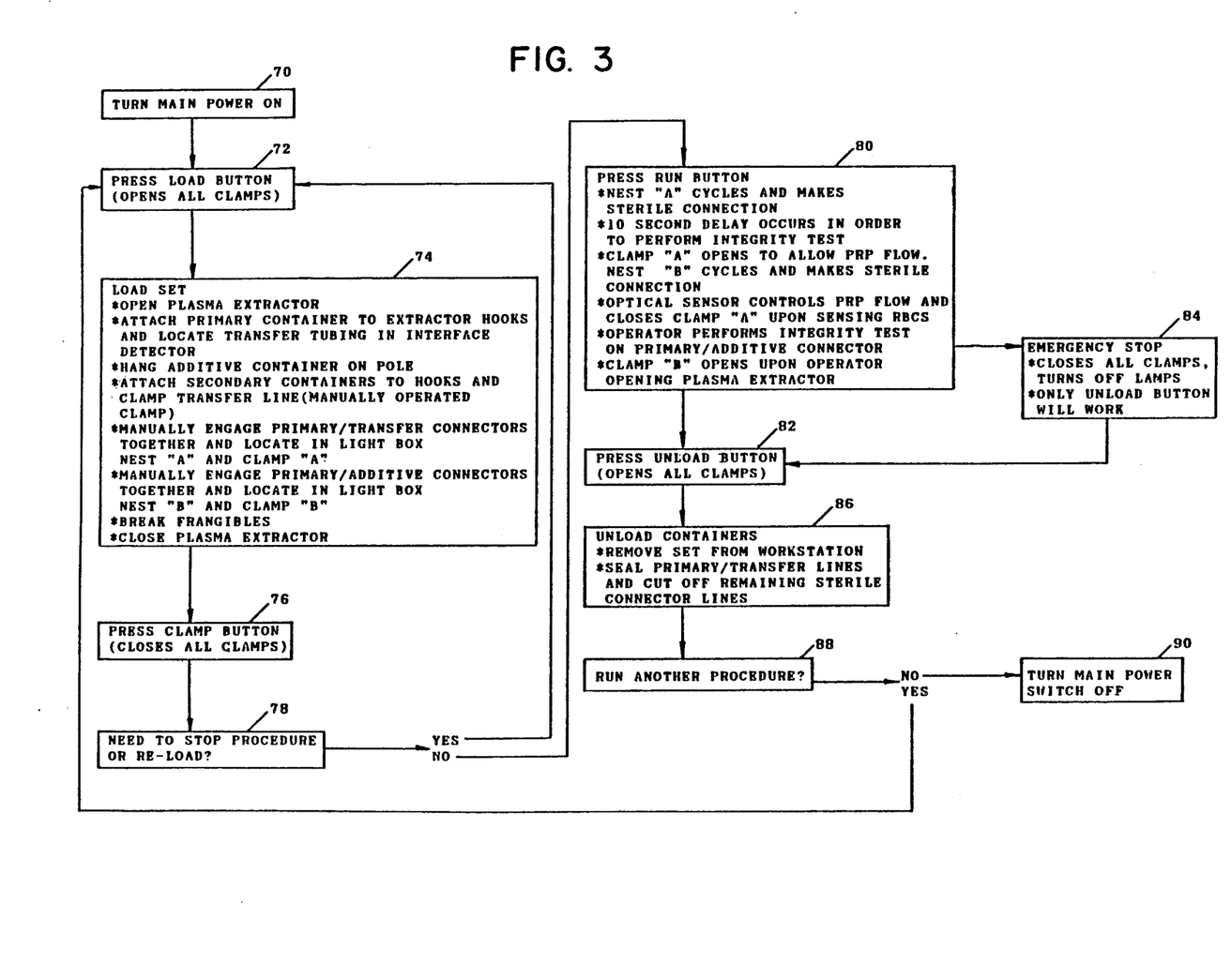
FIG. 3 is a flow diagram illustrating a method in accordance with the present invention.

FIG. 3 illustrates the steps of a method of using the workstation 10 in connection with assemblable packs of the type shown in FIG. 2. With respect to FIG. 3, an operator, in a step 70, first turns the main power on to the workstation 10 by means of an on/off switch 56. Below the on/off switch 56 is an indicator in the plurality 54a indicating power has been turned on. A load button 58 is then depressed, in a step 72, which opens the clamps 26 and 30. A LOAD indicator below the load button 56 in the plurality 54a, is then lite. The clamp 28 could also be opened via the load button 58 if the clamp 28 were a electrically operated solenoid.

In a step 74 the operator loads the desired elements, C1-C4, of the set into the workstation 10. This step includes opening the plasma extractor 24 and inserting the primary container C1 therein and hanging same by the hanger 16. The operator also inserts the tubing T1 into the optical sensor 32. Further the operator would then hang the selected additive container C4 from the hanger 22. The operator would also then join the sterile connectors, such as 40, 42 together positioning them in the light nest 52 and positioning the flexible tubing T5 in the clamp 30. Additionally, in the step 74 the operator would select the appropriate secondary container configuration, such as the containers C2 and C3 of FIG. 2 hanging them from the hangers 18 and 20. The operator would also join the sterile connectors 44, 48 together and position same in the light nest 50. Finally, the tubing T2 would be positioned in the clamp 26. The clamp 28 could also be affixed to the flexible tubing T4 at this time.

In a step 76 the operator would then press the clamp button 60 on the panel 12 which will close the clamps 26 and 30. A CLAMP indicator, located below the clamp button 60, in the plurality 54a, is then lite. At this time the frangibles in the additive containers C4 and C1 can be broken. The plasma extractor 24 can be mechanically released or activated electrically or pneumatically to apply pressure to the primary container C1.

In a step 78 the operator can review the configuration of the set loaded on the workstation 10 to decide whether or not to proceed. If for some reason it is necessary to reload or change one of the elements of the set the operator presses the load button 58 again to reinitiate the load sequence. If the operator is ready to proceed, the run button 62 is depressed and a RUN indicator in the plurality 54a, below the run button 62 is lite. In a step 80 the workstation 10 energizes the light nest 50 to make the sterile connections between the sterile connectors 44, 48. A 10 second delay follows in order that the operator will have an opportunity to perform a Transfer Line Integrity Test. In this test, a movement if any, of the fluid-air interface, in the flexible tubing T2 is detected. Movement of this interface indicates that there may be a leak in the seal between the sterile connectors 44, 48 in the light nest 50. The 10 second delay is arbitrary. It can be made longer or shorter as desired. An indicator 67a is illuminated during this interval indicating that the Transfer Line Integrity Test should now be performed.

Assuming no movement of the fluid-air interface is observed by the operator, the seal has been properly made and the workstation 10 then energizes clamp 26, clamp "A", which opens permitting plasma to flow through the tube T1 through the tube T2 through the tube T3 into the transfer container C2. Plasma continues to flow out of the primary container C1 under the influence of the plasma extractor 24 until red blood cells which are at the bottom of the primary container are forced into the tube T1 and are sensed by the optical sensor 32. As a result of a signal generated by the optical sensor 32, clamp 26 is reclosed. At this time, container C2 includes the platelets and plasma from the primary container C1.

In the same step 80 the light nest 52 is cycled so as to seal the corresponding sterile connectors such as 40, 42. A 10 second delay occurs in order to perform a Line Integrity Test with respect to the seal made in the light nest 52 between the connectors 40, 42. If during this 10 second interval the operator notes a movement of the fluid air interface in the line T1-T5 this is probably due to a failure of the light nest 52 to properly seal the connectors 40, 42. Assuming that no such movement is noted in the tubes T1-T5 the plasma extractor 24 is also opened, and the clamp 30 is deactivated so as to permit the additive from the additive container C4 to flow through the tubes T5 and T1 into the primary container C1. The plasma extractor 24 includes a switch which senses the open or closed condition thereof. Only after the extractor 24 has moved to its - opened position is the clamp 30 opened. An indicator 67d is energized reminding the operator to open the plasma extractor 24 at this time.

In a step 82 the operator then depresses the unload button 64 which opens the clamps 26 and 30. In the step 80 if there is an emergency, the Emergency Stop Button 68 is depressed which closes all clamps, turns off all lamps and enables only the unload button 64. In a step 86 an indicator 67c is energized reminding the operator to place labels on the containers C2 and C3. Labels for the containers C2 and C3 would have, normally, been previously prepared and temporarily attached to the primary container C1. The set including the container C1 through C3 can then be removed from the workstation. Using a conventional RF sealer the line T2 is sealed, and the container C1 can be separated from the containers C2, C3. In a step 88 the operator considers whether or not a further processing step is to be undertaken with respect to the container C2. If not the main power switch 56 is turned off in the step 90. Otherwise the step 72 is repeated.

Figure 4:
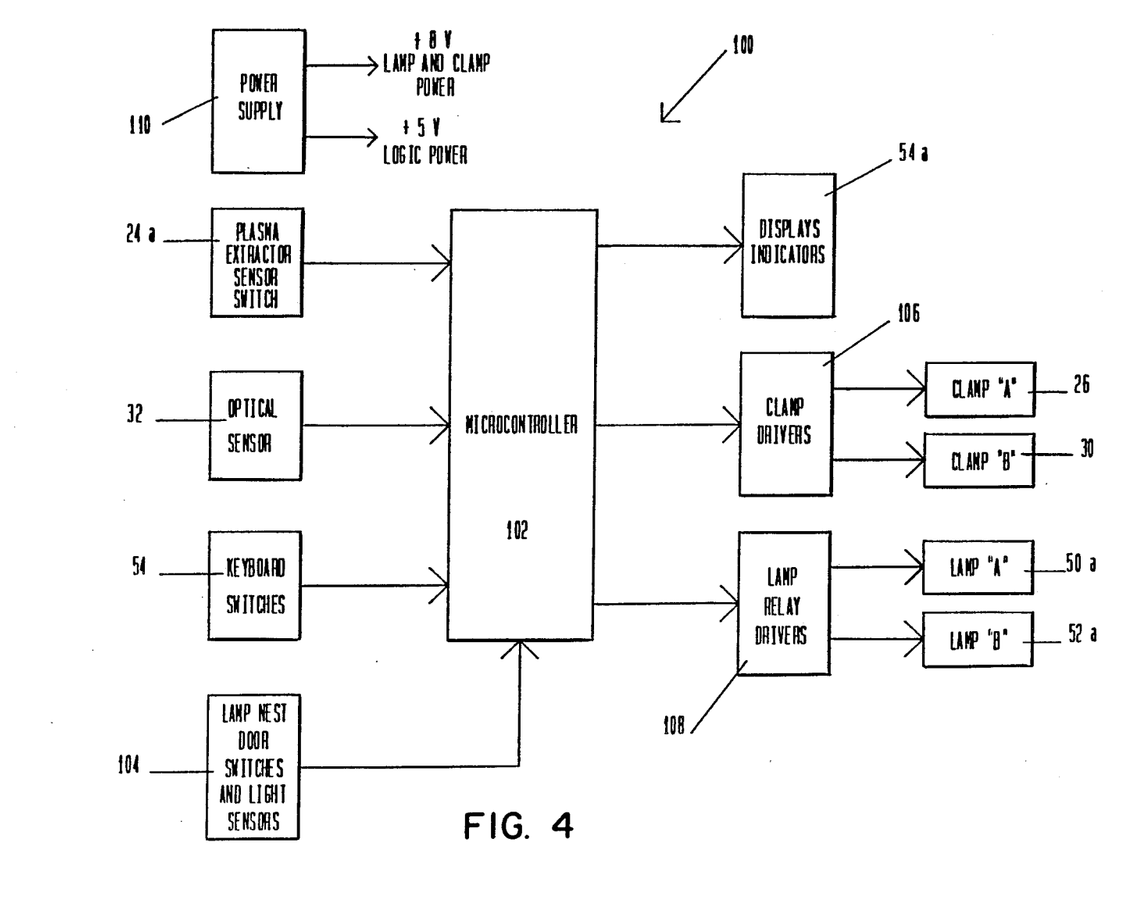
FIG. 4 is a schematic diagram of an electronic circuit in accordance with the present invention.

FIG. 4 is a block diagram schematic of an exemplary set of electronic circuitry usable to implement the steps of the method of FIG. 3. In the circuitry 100 of FIG. 4 a microcontroller or microprocessor 102 which includes both read-only memory and random access memory is operably connected to a status switch 24a which senses the condition of a plasma extractor 24. The controller 102 is also connected to the output of the optical sensor 32, the switches 54 as well as door sensors and radiant energy sensors of the light nests 50 and 52.

In addition, the microcontroller 102 is connected to the plurality of display indicators 54a and 67, drivers 106 for the clamps 26 and 30 and drivers 108 for a lamp A, 50a, in light nest 50 and a lamp B, 52a, in light nest 52. A power supply 110 is operably connected to the electronic circuitry as is conventional.

A stored program in the microcontroller 102 implements the method steps in the flow diagram of FIG. 3.

The workstation 10 can also include a variety of options. These include, the automatically activated plasma extractor referred to previously, automatic sensing of movement of the fluid-air interface during Line Integrity Tests, other forms of leak sensors operative to sense the integrity of the seals between sterile connectors such as the connectors 40, 42 or 44, 48; a solenoid actuated clamp on the line T4 can replace the manually operable clamp 28, a scale to weigh the plasma in the primary container C1, and an RF tubing sealer could be mounted on the workstation 10. Another set of clamps and a light nest could also be added to the workstation 10, above the container C2 into which the platelets are transferred to provide for flow connection to a bag of additive for the platelets. This second bag of additives could be added to the container C2, and the platelets therein after the plasma and platelets have been centrifuged and the plasma expressed into the container C3.

Figure 5:
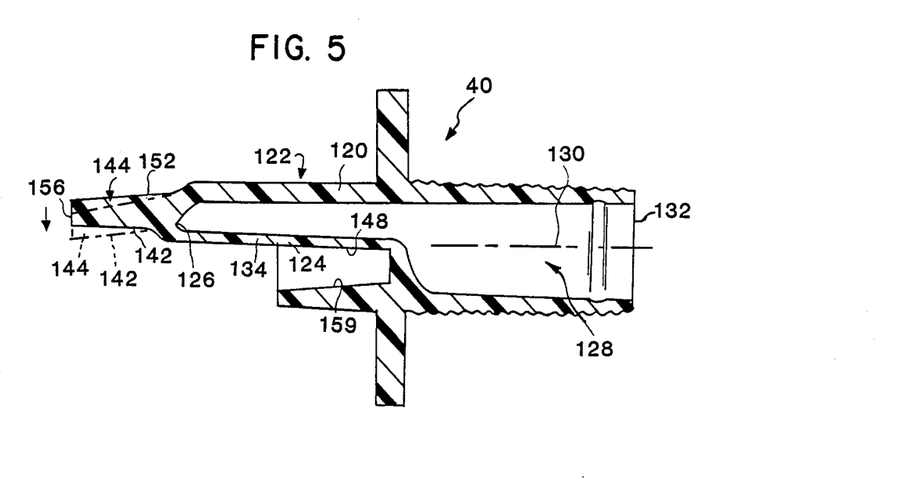
FIG. 5 is a side sectional view of an exemplary sterile connector usable in the embodiment of the present invention.

With respect to the sterile connectors, such as the connectors 40, 42, 44, 46 or 48 of FIG. 2, FIG. 5 illustrates in further detail the structure thereof as taught by the above noted, incorporated patent application.

As disclosed in FIG. 5, a sidewall 120 of a tubular body 122 of each connector such as connectors 40, 42, 44, 46 or 48 includes a generally planar surface portion 124. The surface portion 124 extends rearwardly from a closed end 126 of a bore 128 in a plane which is generally parallel to axis 130 of the bore 128. An opening 132 at the rear of the exemplary connector 40 permits fluid to flow through the connector to or from an attached flexible conduit such as the conduit T5 attached to the connector 40.

While various configurations can be used, due to the particular position of the planar surface portion 124 in the illustrated embodiment, the internal dimension of the bore 128 adjacent to its closed end 126 is about one-half the internal dimension of the bore 128 adjacent its open end 132.

The planar surface portion 124 includes a region 134 which, when heated, is meltable to form an opening communicating with the bore 128. Fluid can be conducted through this formed opening. The meltable region 134 is generally centered along a centerline axis 136 of the planar surface portion 124 (see FIG. 6). The meltable region 134 is also preferably positioned in close proximity to the closed end 126 of the bore 128 to minimize the size of the area between the formed opening and the closed bore end 126, in which fluid can become entrapped.

Figure 6:
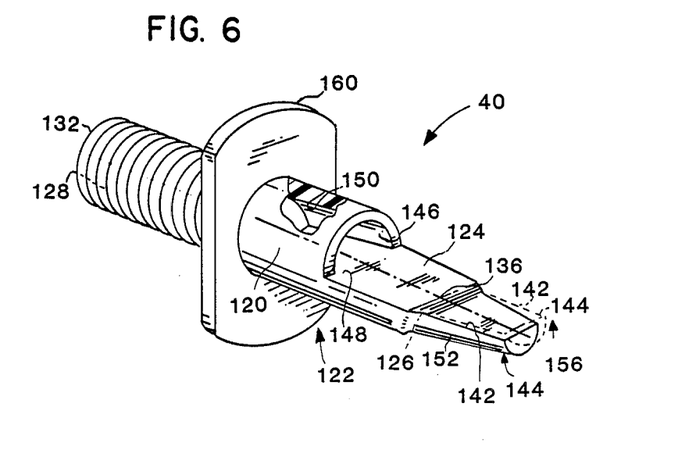
FIG. 6 is a perspective view, partly broken away, of the sterile connector of FIG. 5.

The region 134 preferably melts only at temperatures which result in the destruction of bacterial contaminants, i.e., over 200° C. In this preferred arrangement, the region 134 can be opened only in connection with an active sterilization step which serves to sterilize the regions adjacent to the fluid path as the fluid path is formed.

When two connectors such as 40 and 42 are joined, the meltable regions 134 of the two connectors 40 and 42 are aligned and placed in intimate facing contact. When jointly heated, both of the regions 134 melt, fusing the two connectors 40 and 42 together. A fluid path 140 (see FIG. 8) is also opened between the two connectors 40 and 42, and thus between the attached conduits T5 and T1.

As best shown in FIG. 6, while a planar tab surface 142 is generally parallel to the planar body surface portion 124, the two surfaces 142 and 124 are themselves not coplanar. Instead, the planar tab surface 142 is offset in the direction of the bore 128 away from the planar body surface portion 124.

As shown by arrows and in phantom lines in FIGS. 5 and 6, a tab 144 of each connector such as 40 and 42 is resiliently deformable relative to the body 122 out of its normal position in response to external force in a direction transverse of the axis 136.

The interior configuration of a slot 146, like the exterior configuration of the tab 144, constitutes a cone which has been truncated in two planes. The slot 146 thus includes a generally planar surface 148, the axis 136 of which is centered along the planar surface 124 (see FIG. 6), as well as an arcuate surface 150, which extends radially outwardly from the axis 136 and which tapers toward the axis 136 in a direction toward the open end 132 of the bore 128. The slope and taper of the arcuated surface 150 correspond with the slope and taper of an external arcuate tab surface 152.

The tab 144 of the connector 40 will thus uniquely mate with the slot 146 of the connector 42, and vice versa, but only when the centerline 136 of the tab 144 and slot 146 are aligned. When the centerlines 136 do not align, the tab 144 and slot 146 do not mate. Instead, a planar end surface 156 of the tab 144 abuts against the entrance of the slot 146.

Figure 7:
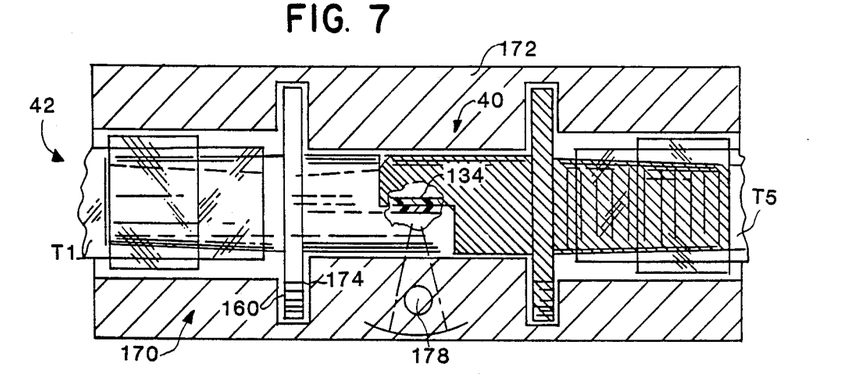
FIG. 7 is a perspective view, partly broken away and in section, of two sterile connectors joined together in an apparatus for applying radiant energy thereto.

As shown in FIG. 7, a device 170 can be used to generate the melting energy. The device 170 includes a base 172 having a pair of spaced apart holders 174. The holders 174 jointly receive a collar 160, but only when the collars 160 are spaced apart the same distance as the holders 174. By purposeful design, when the meltable regions 134 are not in the desired registration, the collars 160 are spaced either farther or closer apart than the holders 174. Thus, when the meltable regions 134 are not in the desired registration, the connectors, such as the connectors 40 and 4, cannot be physically mounted in the device 170.

The type of energy employed to melt the region 134 of the planar surface 124 can vary. For example, thermal conduction can be used as disclosed in the above-noted U.S. Pat. No. 4,022,256. In this arrangement (not shown), the energy source constitutes a heat plate or the like in contact with the body 122 of at least one of the connectors 40 or 42. The body 122 of the connector 40 would, in this embodiment, be made of a thermosetting or high melt point material which would conduct heat energy from the source to the engaged meltable regions 134. The meltable regions 134 would be made of a material having a lower melting temperature than the body 122. The conducted energy would thus melt only the region 134, not the surrounding body 122.

In the illustrated and preferred embodiment, however, thermal radiation is used to heat the meltable region 134. In this arrangement, the body 122 of each of the connectors 40 and 42 is made entirely of a thermoplastic material which can be molded by conventional means. The meltable region 134 of at least one of the connectors 40 and 42 includes a radiant energy absorbing material which is intermixed with or applied upon the surface of the thermoplastic body material. By applying a sufficient amount of radiant energy, the radiant energy absorbing region 134 is heated until melting occurs. An opening is formed in the region 134. Fluid communication is thereby opened with the associated conduit via the region 140.

As used herein, the term "radiant energy" broadly refers to energy which is in the form of electromagnetic waves, such as radio waves, infrared waves, visible light, ultraviolet waves, x-rays and the like. Because the transfer of radiant energy requires no intervening medium, the transfer can be faster and more efficient than in conductive or convected heat transfer, both of which require an intervening medium.

Because, in the illustrated and preferred embodiment, thermal radiation is the means employed to heat the overlying regions 134, the body 122 of at least one of the connectors 40 or 42 must be capable of transmitting the radiant energy to the meltable regions 134 of the connector.

Figure 8:
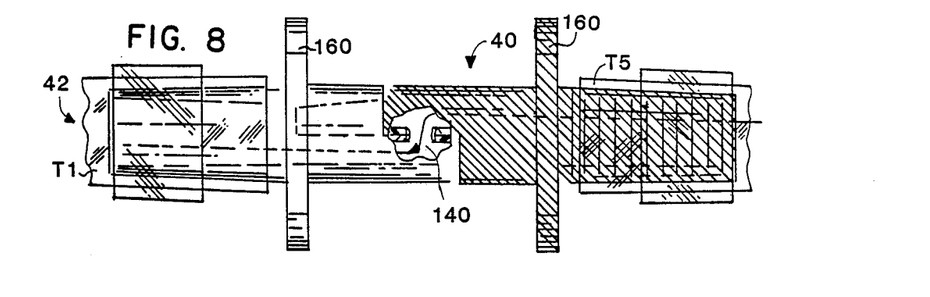
FIG. 8 is a planar view partly broken away, of two exemplary sterile connectors that have been fused together.

In the illustrated embodiment, the thermoplastic body 122 of the one connector 40 can be made uniformly absorbent (i.e., opaque to) the applied radiant energy (see FIGS. 7 and 8). The thermoplastic body 122 of the other connector 42 can be made of a material which absorbs the applied radiant energy in lesser amounts than the opaque material of the connector 40. Preferably, the entire body 122 of this connector 42 is relatively nonabsorbant of (i.e., transparent to) the particular type of radiant energy which will be applied.

In this arrangement, as shown in FIG. 7, after the connectors 40 and 42 are fitted into the device 170, radiant energy is applied from a source 178 to the assembly 40 and 42 through the transparent body 122 of the connector 42 and focused upon the meltable regions 134. The source 178 comprises an incandescent quartz lamp which has a tungsten filament operating at about 3150° K. This lamp emits radiant energy which lies in a continuous band encompassing mostly infrared and visible energy, although some ultraviolet radiation is included.

The transparent body 122 is itself not heated to any great extent by the radiant energy. However, in response to the applied thermal radiation, the meltable region 134 of the opaque connector 40 is heated to a temperature sufficient to melt the opaque region 134.

Because, in accordance with the invention, the regions 134 are held in intimate contact, the thermoplastic (i.e., meltable) region 134 of the transparent connector 42 conducts heat from the opaque region 134 in sufficient quantities to also melt. As a result, the regions 134 jointly melt and fuse together.

In the process of melting, the regions 134 form the opening 140 (see FIG. 8) which establishes through the coupled connectors 40 and 42 a fluid path which is hermetically sealed about its periphery.

Because, in accordance with the invention, the coupling means 146 assures the proper alignment between the meltable regions 134, the formed opening is uniform with respect to each region 134, lying along the centerline 136 of each planar surface portion 124.

The particular materials selected for the connectors 40 and 42 depend largely upon the type of radiant energy which is to be applied.

In the illustrated embodiment, in which infrared and visible light are used, the connectors, such as the connectors 40 and 42, can be made of a material fabricated from poly(4-methyl-1-pentene), which is sold under the trademark TPX by Mitsui Chemical Company. This thermoplastic materials has a crystalline melting point of approximately 235° C. and is further discussed in Boggs et al U.S. Pat. No. 4,325,417.

The opaque connector 40 includes, intermixed with the TPX material, a charcoal filler. It thus absorbs radiant energy in the infrared and visible light band. The TPX material of the transparent connector 42 is free of the filler and is relatively transparent to (i.e., generally nonabsorbent of) this band of radiant energy.

Figure 9:
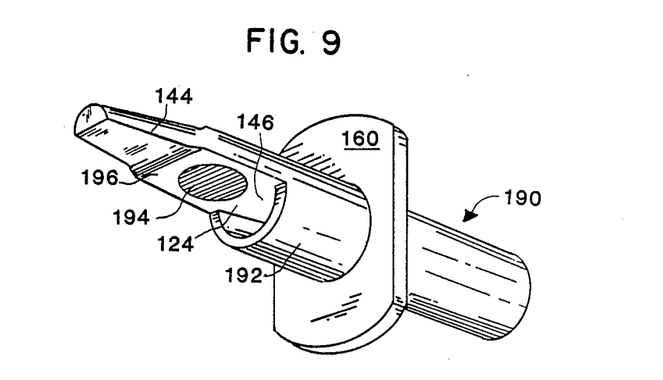
FIG. 9 is a view in perspective of another exemplary sterile connector.

Alternately, as shown in FIG. 9, instead of using the opaque connector such as shown in FIGS. 5 or 6, a connector 190 can be used. The connector 190 has a body 192 which is uniformly transparent to the passage of the applied radiant energy, like the body of the connector 42 as just described. However, in this arrangement, a radiant energy absorbing material 194 is affixed on the external surface of a meltable region 196, for example by hot stamping, printing, gluing, and the like. As before described, thermal radiation will heat the material 194 and cause the region 96 to melt.

Two of the connectors 190 can be coupled together to form an assembly with the applied meltable regions 194 position in intimate facing contact. The fusing apparatus 70 of FIG. 7 can then be used to fuse the two connectors together.

The size of the mating connectors, such as the connectors 40 and 42, can vary according to the intended field of use. In a representative embodiment, the overall length of each connector such as 40 or 42 is approximately 1.4 inches, and the maximum outside diameter, exclusive of the collar 160, is about 0.3 inch. In this arrangement, the tab 144 extends about 0.261 inch outwardly from the closed end 126 of the bore 128. Both the tab 144 and the slot 146 have an accurate surface, respectively 152 and 159, with an approximate slope of 5°. The arcuate surface 152 of the tab 144 has an arc of approximately 0.092 inch radius adjacent to the planar end surface 156. The planar surface 148 of the slot 146 has an arc of approximately 0.112 inch radius at the entrance of the slot 146. The planar surface 142 of the tab 144 is offset from the planar surface portion 124 of the body 122 by about 0.003 inch. In this arrangement, an approximately 0.0012 inch interference fit develops between the tab 144 and slot 146 when the meltable regions are in proper registration.

While a particular embodiment of the invention has been described herein it will be understood that the broader aspects of the invention include the use of all types of connectors as may be utilized to provide a sterile flow between the various containers. The actual size, shape or method of sealing the connectors together is not a limitation of the present invention. The use of all forms of heat or radiant energy to seal two sterile connectors together come within the scope of the present invention. Additionally, the broader aspects of the invention include those electrical components as would be known to one of skill in the art including those additional sensors or electronic elements as could be used to further automate the steps of the present method.

We claim:

1. A fluid transfer work station usable with separate first and second connector carrying modular containers for the processing of a selected fluid previously accumulated in the first container, the work station comprising:

planar supporting means bounded at least in part by selectively shaped spaced-apart edge members;

first and second hangers carried by said supporting means, spaced-apart thereon between said edge members for supporting respectively the first and second containers;

spring activated means connected to said supporting means between said edge members and adjacent to said first hanger, for compressing the first container;

electrically actuated means, affixed to said supporting means between said edge members, for fixedly coupling the connector of the first container to the connector of the second container and forming a fluid flow path therebetween;

means, affixed to said supporting means adjacent said first hanger, for sensing a flow of fluid from the first container in response to said spring activated means compressing the first container;

electrically activated clamping means, affixed to said supporting means adjacent said coupling means, for blocking a flow of fluid from the first container to the second container; and programmed control means coupled to said coupling means, said sensing means and said clamping means for sequentially actuating said coupling means thereby coupling the first container to the second container, detecting a selected, sensed flow of fluid from the first container to the second container and in response thereto enabling said clamping means to block same.

2. A work station as in claim 1 including:
   manually operable switch means for releasing said clamping means.

3. A work station as in claim 1 usable with a connector carrying container of additive where the first container carries a second connector, the work station including:

means for supporting the additive container adjacent said planar means relative to said first hanger for draining the contents of the additive container into the first container;

second electrically actuated means, affixed to said supporting means between said edge members, for fixedly coupling the second connector for the first container to the connector for the container of additive and forming a fluid flow path therebetween;

second electrically activated clamping means, affixed to said planar member, adjacent to said second coupling means, for blocking a flow of fluid from the container of additive to the first container; and said programmed control means coupled to said second coupling means and said second clamping means and including means for activating said second coupling means subsequent to said second clamping means blocking fluid flow between the container of additive and the first container.

* * * * *